(12) United States Patent
Dria et al.

(10) Patent No.: US 7,220,440 B2
(45) Date of Patent: *May 22, 2007

(54) METHOD FOR REDUCTION OF ACRYLAMIDE IN ROASTED COFFEE BEANS, ROASTED COFFEE BEANS HAVING REDUCED LEVELS OF ACRYLAMIDE, AND ARTICLE OF COMMERCE

(75) Inventors: Glenn James Dria, Okeana, OH (US); David Vincent Zyzak, Mason, OH (US); Roger William Gutwein, Cincinnati, OH (US); Francisco Valentino Villagran, Mason, OH (US); Herbert Thomas Young, Cincinnati, OH (US); Paul Ralph Bunke, Cincinnati, OH (US); Peter Yau Tak Lin, Liberty Township, OH (US); John Keeney Howie, Oregonia, OH (US); Richard Gerard Schafermeyer, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/603,973

(22) Filed: Jun. 25, 2003

(65) Prior Publication Data
US 2004/0081724 A1    Apr. 29, 2004

Related U.S. Application Data

(60) Provisional application No. 60/431,150, filed on Dec. 5, 2002, provisional application No. 60/421,344, filed on Oct. 25, 2002.

(51) Int. Cl.
A23F 5/16 (2006.01)
A23F 5/18 (2006.01)

(52) U.S. Cl. .......................... 426/45; 426/432; 426/629

(58) Field of Classification Search ................. 426/45, 426/106, 594, 595, 596, 629, 656, 430, 431, 426/432
See application file for complete search history.

(56) References Cited

U.S. PATENT DOCUMENTS

| | | | |
|---|---|---|---|
| 2,490,431 A | 12/1949 | Green et al. | |
| 2,704,257 A | 3/1955 | De Sollano et al. | |
| 2,759,832 A | 8/1956 | Cording et al. | |
| 2,780,552 A | 2/1957 | Willard et al. | |
| 2,905,559 A | 9/1959 | Andersen et al. | |
| 3,085,020 A | 4/1963 | Backinger et al. | |
| 3,369,908 A | 2/1968 | Gonzales et al. | |
| 3,690,895 A | 9/1972 | Amadon et al. | |
| 3,917,866 A | 11/1975 | Purves et al. | |
| 3,987,210 A | 10/1976 | Cremer | |
| 3,998,975 A | 12/1976 | Liepa | |
| 4,210,594 A | 7/1980 | Logan et al. | |
| 4,983,408 A * | 1/1991 | Colton ........................ | 426/45 |
| 4,985,269 A | 1/1991 | Irvin et al. | |
| 5,356,646 A | 10/1994 | Simic Glavaski et al. | |
| 5,464,642 A | 11/1995 | Villagran et al. | |
| 5,464,643 A | 11/1995 | Lodge | |
| 5,558,886 A | 9/1996 | Martinez-Bustos et al. | |
| 6,066,353 A | 5/2000 | Villagran et al. | |
| 6,068,873 A | 5/2000 | Delrue et al. | |
| 6,287,622 B1 | 9/2001 | Villagran et al. | |
| 6,528,768 B1 | 3/2003 | Simic-Glavaski et al. | |
| 2004/0058054 A1* | 3/2004 | Elder et al. ................. | 426/658 |

FOREIGN PATENT DOCUMENTS

| | | | |
|---|---|---|---|
| JP | 63-196236 | * | 8/1988 |
| WO | WO 96/01572 | | 1/1996 |
| WO | WO 01/91581 | | 12/2001 |
| WO | WO2004/004484 | | 1/2004 |

OTHER PUBLICATIONS

FAO/WHO Consultation on the Health Implications of Acrylamide in Food: Summary Report; Geneva Switzerland, Jun. 25-27, 2002.
Talburt & Smith; "Potato Processing"; 4th Edition, 1987, pp. 535-646.
Watson, S.A.; "Corn: Chemistry and Technology"; American Association of Cereal Chemists, 1987; pp. 410-420.
Zyzak, David A. et al.; "Acrylamide Formation Mechanism in Heated Foods"; Journal of Agricultural and Food Chemistry; vol. 51, No. 16, pp. 4782-4787, (Jul. 2003).
Biederman, Maurus, et al.; "Methods for Determining the Potential of Acrylamide Formation and Its Elimination in Raw Materials for Food Preparation, such as Potatoes"; Official Food Control Authority of the Canton of Zurich, date n.a.
Biederman, Maurus, et al.: "Experiments on Acrylamide Formation and Possibilities to Decrease the Potential of Acrylamide Formation in Potatoes"; Official Food Control Authority of the Canton of Zurich, date n.a.

(Continued)

Primary Examiner—Keith Hendricks
(74) Attorney, Agent, or Firm—Ingrid N. Hackett; Melody A. Jones; Kim W. Zerby

(57) ABSTRACT

Roasted coffee beans having reduced levels of acrylamide, coffee beans having reduced levels of asparagine, and an article of commerce. In one aspect, the invention provides a method for reducing the level of acrylamide in roasted coffee beans comprising reducing the level of asparagine in coffee beans. In another aspect, the invention provides a method for reducing the level of asparagine in coffee beans comprising adding an asparagine-reducing enzyme to coffee beans. In still another aspect, an article of commerce communicates to the consumer that the roasted coffee beans, coffee beans, product comprising roasted coffee beans or coffee beans, and/or article of commerce has reduced or low levels of asparagine and/or acrylamide.

2 Claims, 3 Drawing Sheets

OTHER PUBLICATIONS

Nielsen, Monk; "Enzyme Technology For Production of Protein Based Flavours"; Novo Nordisk; 1995.

www.Foodstandards.gov.uk; "Food Standards Agency Study of Acrylamide in Food Background Information and Research Findings"; Press Briefing 17.05.02, 2002.

European Commission; Health & Consumer Protection Directorate—General; "Opinion of the Scientific Committee on Food on new findings regarding the presence of acrylamide in food"; Jul. 3, 2002.

Institute of Food Science & Technology (UK); "Additional Research on Acrylamide in Food Essential, Scientists Declare"; Joint Press Release FAO/WHO/51; Jun. 27, 2002.

www.cspinet.org: Center for Science in the Public Interest; "New Tests Confirm Acrylamide in American Foods"; Jun. 25, 2002.

Tareke, Eden, et al.; "Analysis of Acrylamide, a Carcinogen Formed in Heated Foodstuffs"; Journal of Agricultural and Food Chemistry, pp. A-I, date n. a.

Sanders, R.A., et al.; "AN LC/MS Acrylamide Method and It's Use in Investigating the Role of Asparagine"; Presented at the Association of Analytical Communities ; Sep. 2002.

Zyzak, David; "Acrylamide: Mechanism of Formation in Heated Foods": Presented to the FDA Food Advisory Committee; Feb. 24, 2003.

* cited by examiner

Figure 2 Mode of action for asparaginase

METHOD FOR REDUCTION OF ACRYLAMIDE IN ROASTED COFFEE BEANS, ROASTED COFFEE BEANS HAVING REDUCED LEVELS OF ACRYLAMIDE, AND ARTICLE OF COMMERCE

CROSS REFERENCE TO RELATED APPLICATIONS

This application claims the benefit of priority to U.S. Provisional Application Ser. No. 60/421,344, filed Oct. 25, 2002, and to U.S. Provisional Application Ser. No. 60/431,150, filed Dec. 5, 2002, all of which are herein incorporated by reference.

FIELD OF INVENTION

The present invention relates to the reduction of acrylamide in roasted coffee beans, the reduction of asparagine in coffee beans, roasted coffee beans having reduced levels of acrylamide, and coffee beans having reduced levels of asparagine. The invention further relates to an article of commerce.

BACKGROUND OF THE INVENTION

With over 400 billion cups consumed every year, coffee is the world's most popular beverage. Although coffee has been enjoyed for thousands of years, researchers have only recently discovered that coffee contains acrylamide. In April 2002, the Swedish National Food Administration and researchers from Stockholm University announced their findings that acrylamide, a potentially cancer-causing chemical, is formed in many types of foods and beverages that undergo heat processing. Acrylamide has a carcinogenic potency in rats that is similar to that of other carcinogens in food, but for humans, the relative potency in food and beverages is not known. Only limited human population data are available for acrylamide and these provide no evidence of cancer risk from occupational exposure. (*FAO/WHO Consultation on the Health Implications of Acrylamide in Food: Summary Report*; Geneva, Switzerland, 25-27 Jun. 2002.)

Although further research is needed to assess what health effects, if any, may result from human consumption of acrylamide at the levels commonly found in roasted coffee products, many consumers have voiced concern. Accordingly, it is an object of the present invention to provide a method for reducing the level of acrylamide in roasted coffee beans. It is also an object of the present invention to provide roasted coffee beans having reduced levels of acrylamide. Further, it is an object of the present invention to provide an article of commerce that communicates to the consumer that a roasted coffee product has reduced or low levels of acrylamide.

SUMMARY OF THE INVENTION

In one aspect, the present invention provides a method for reducing the level of acrylamide in roasted coffee beans. In one embodiment, the method comprises adding an asparagine-reducing enzyme to coffee beans.

In another aspect, the present invention provides a method for reducing the level of asparagine in coffee beans. In one embodiment, the method comprises adding an asparagine-reducing enzyme to coffee beans.

In another aspect, the present invention provides roasted coffee beans having reduced levels of acrylamide.

In another aspect, the present invention provides coffee beans having reduced levels of asparagine.

In yet another aspect, the present invention provides an article of commerce that communicates to the consumer that a product comprising roasted coffee beans has reduced or low levels of acrylamide.

In still another aspect, the present invention provides an article of commerce that communicates to the consumer that a product comprising coffee beans has reduced or low levels of asparagine.

All documents cited herein are, in relevant part, incorporated herein by reference; the citation of any document is not to be construed as an admission that it is prior art with respect to the present invention.

As used herein, all percentages (%) are by weight unless otherwise indicated.

BRIEF DESCRIPTION OF THE DRAWINGS

FIG. 1 sets forth the proposed reaction mechanism by which acrylamide forms from asparagine and a carbonyl source (such as glucose). $R_1$ and $R_2$ can=H, $CH_3$, $CH_2OH$, $CH_2(CH_2)_nCH_3$, or any other component making up a reducing sugar; n can be any integer less than 10.

FIG. 2 sets forth the proposed reaction mechanism by which asparaginase reacts with asparagine to prevent the formation of acrylamide.

FIG. 3 sets forth a sample chromatogram for LC analysis of asparagine and aspartic acid. The x-axis represents retention time and the y-axis represents response.

DETAILED DESCRIPTION OF THE INVENTION

Applicants have discovered that asparagine, a naturally occurring amino acid found in virtually all living systems, can form acrylamide when heated. Thus, materials richer in asparagine, when heated, tend to contain higher levels of acrylamide; this is especially the case when asparagine-containing materials are heated in the presence of reducing sugars.

Figure 1:
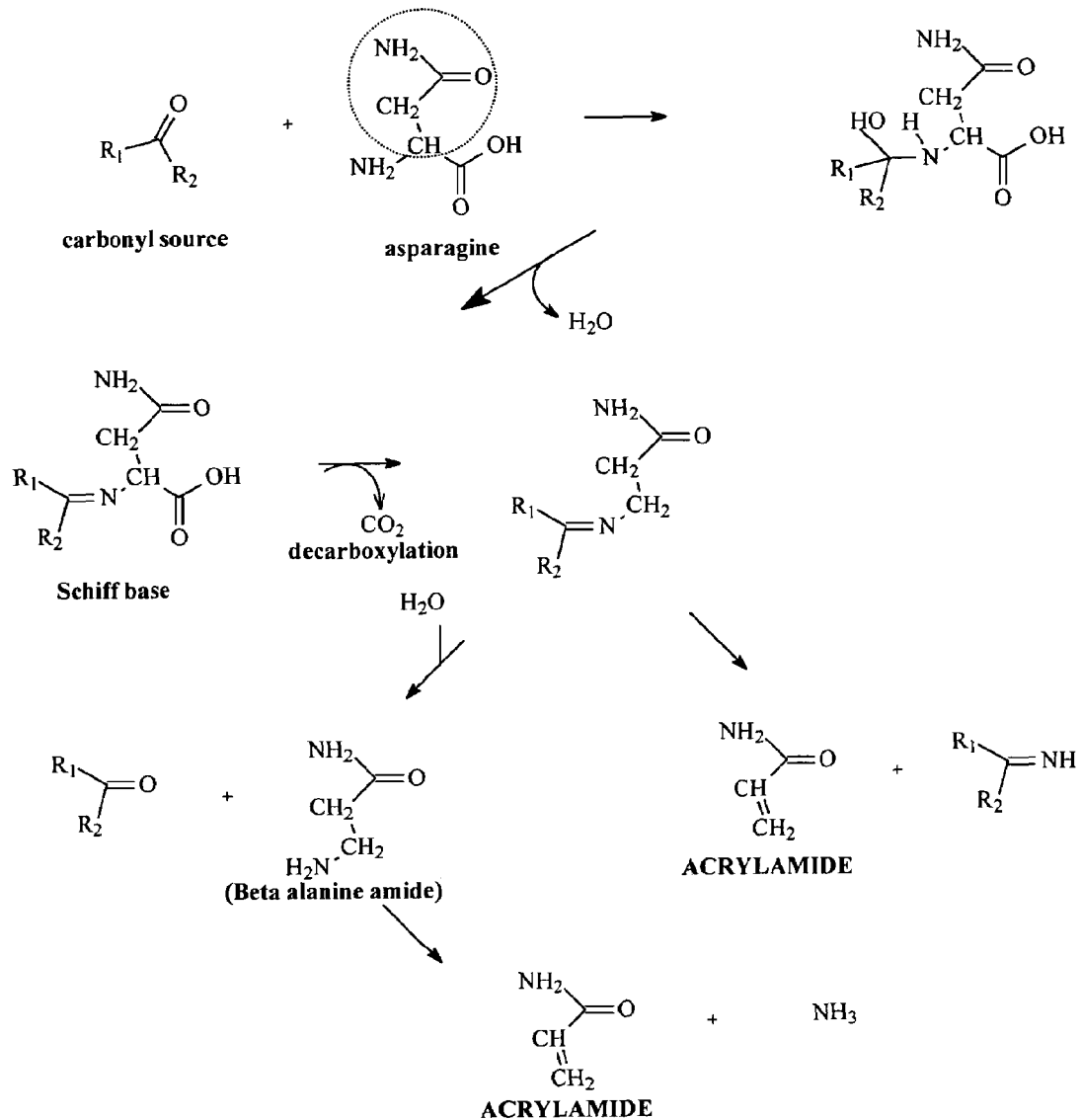
FIG. 1.

While not being limited by theory, it is believed that acrylamide forms via the reaction mechanism set forth in FIG. 1. It is believed that the alpha-amine group of free asparagine reacts with a carbonyl source, forming a Schiff base. Under heat, the Schiff base adduct decarboxylates, forming a product that can either: (1) hydrolyze to form beta-alanine amide (which can, under heat, further degrade to form acrylamide) or (2) decompose to form acrylamide and the corresponding imine. (Applicants have discovered that the circled precursor atoms comprise the carbons and nitrogens in acrylamide.)

Accordingly, Applicants have further discovered that acrylamide formation in roasted coffee beans can be reduced by removing the asparagine or converting the asparagine in the coffee beans to another substance before final roasting of the beans. When such beans containing reduced levels of asparagine undergo final roasting, the amount of acrylamide formed is reduced.

Figure 2:
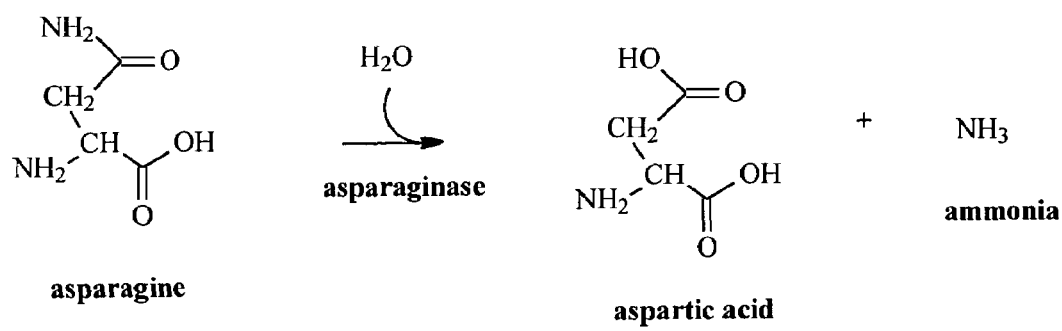
FIG. 2.

Applicants have found that adding an enzyme that hydrolyzes the amide group on the side chain of asparagine prior to final roasting of the coffee beans reduces the level of acrylamide present in the roasted coffee beans. While not being limited by theory, it is believed that the addition of such an enzyme degrades the side chain of asparagine, thus preventing the asparagine from forming acrylamide. In doing so, the amide bond is hydrolyzed and asparagine is converted to aspartic acid. This reaction mechanism is set forth in FIG. 2.

Preferred enzymes for use in the method herein include, but are not limited to, asparaginase. However, any enzyme capable of hydrolyzing the amide group of free asparagine to prevent the formation of acrylamide is within the scope of the present invention.

The advantages of using enzymes are numerous. These advantages include: (a) they are natural, nontoxic substances; (b) they generally catalyze a given reaction without causing unwanted side reactions; (c) they are active under very mild conditions of temperature and pH; (d) they are active at low concentrations; (e) the rate of reaction can be controlled by adjusting temperature, pH, and the amount of enzyme employed; and (f) they can be inactivated after the reaction has proceeded to the desired extent. (*Food Chemistry*, 4th Ed., Owen R. Fennema, Ed., Marcel Dekker, Inc., New York, 1985, pp. 427, 433.)

A. Method for Reduction of Acrylamide in Roasted Coffee Beans

In one aspect, the present invention provides a method for the reduction of acrylamide in roasted coffee beans. In one embodiment, the method comprises reducing the level of asparagine in coffee beans. In another aspect, the method comprises adding an asparagine-reducing enzyme to coffee beans. The preferred enzyme is asparaginase.

In a preferred embodiment, the present invention provides a method for reducing the level of acrylamide in roasted coffee beans, comprising:

(1) providing coffee beans containing asparagine;
(2) optionally pre-treating the coffee beans;
(3) adding an asparagine-reducing enzyme to the coffee beans;
(4) allowing a sufficient time for the enzyme to react with the asparagine;
(5) optionally deactivating or optionally removing the enzyme; and
(6) roasting the coffee beans to form roasted coffee beans.

In another aspect, the present invention provides a method for the reduction of asparagine in coffee beans. In one embodiment, the method comprises adding an asparagine-reducing enzyme to coffee beans. The preferred enzyme is asparaginase.

In a preferred embodiment, the present invention provides a method for reducing the level of asparagine in coffee beans, comprising:

(1) providing coffee beans containing asparagine;
(2) optionally pre-treating the coffee beans;
(3) adding an asparagine-reducing enzyme to the coffee beans;
(4) allowing a sufficient time for the enzyme to react with the asparagine; and
(5) optionally deactivating or optionally removing the enzyme.

1. Providing Coffee Beans Containing Asparagine

Coffee beans are the seeds of cherries which grow from coffee trees in a narrow subtropical belt around the world. There are many coffee species, however, it is generally recognized that there are two primary commercial coffee species: *Coffea arabica* and *Coffea canephora* var. *robusta*. Coffees from the species *arabica* are described as "Brazils," which come from Brazil, or "Other Milds" which are grown in other premium coffee producing countries. Premium *arabica* countries are generally recognized as including Colombia, Guatemala, Sumatra, Indonesia, Costa Rica, Mexico, United States (Hawaii), El Salvador, Peru, Kenya, Ethiopia and Jamaica. Coffees from the species canephora var. *robusta* are typically used as a low cost extender or as a source of additional caffeine for *arabica* coffees. These *robusta* coffees are typically grown in the lower regions of West and Central Africa, India, South East Asia, Indonesia, and Brazil. After the coffee cherries are harvested, the fruit is typically removed from the seed.

Any suitable coffee beans, including mixtures of various types of beans, can be used in accordance with the present invention. The preferred coffee beans are *arabica, robusta*, or a mixture thereof.

As used herein, the term "coffee beans" or "beans" includes coffee beans in any suitable form. Non-limiting examples include coffee beans in bean form or in the form of a green coffee bean extract (e.g., dry or wet green coffee bean extracts). The coffee beans can be whole or can be reduced in particle size. The size of the coffee beans can be reduced by cracking, chopping, dicing, macerating, grinding, flaking, or any other suitable method. The size of the coffee beans may be reduced at any suitable stage of the method, including any time before, during, or after the addition of the asparagine-reducing enzyme, but before the end of the time period in which the enzyme is allowed to react with the coffee beans.

Furthermore, the coffee beans for use herein optionally, but preferably, have their fruits removed. In one embodiment, coffee beans that have undergone decaffeination are used. In another embodiment, coffee beans that have not undergone decaffeination are used. In still another embodiment, a mixture of decaffeinated and un-decaffeiniated beans is used. Preferably green coffee beans are used, but any suitable beans that have not been subjected to final roasting can be utilized in accordance with the method herein.

2. Optionally Pre-Treating the Coffee Beans

The coffee beans may optionally be pre-treated before or during the addition of enzyme. Suitable pre-treatment includes drying, hydrating, rinsing without or with mechanical action (e.g., wet-brushing), pressurizing, steaming, blanching, heating, reduced pressure processing (e.g., vacuum), particle size reduction, or combinations thereof. Suitable pre-treatment methods can also include the exposure of the coffee beans to one or more cellulose-degrading enzymes; this method can be used alone or in combination with one or more other pre-treatment methods. Preferred cellulose-degrading enzymes include cellulase, hemicellulase, pectinase, and mixtures thereof, although any suitable cellulose-degrading enzyme can be used.

Pre-treatment can facilitate removal and/or extraction of the asparagine from inside the beans, allowing the asparagine to be brought into more intimate contact with the asparagine-reducing enzyme outside of the beans. Pre-treatment can also facilitate the migration of asparagine-reducing enzyme into the beans, allowing for more intimate contact with the asparagine-reducing enzyme inside of the beans, as well as more uniform distribution of asparagine-reducing enzyme within the bean.

The beans can be dried to open up their pores. In one embodiment, the beans are dried in preparation for soaking in an asparagine-reducing enzyme solution. Drying creates a driving force for the enzyme solution to penetrate the beans, and thus for the enzyme to reach the beans' interior. Any suitable means of drying the beans may be used, as long as the drying method employed does not reach a temperature where asparagine could start reacting to form significant levels of acrylamide. Preferably, drying methods employing temperature below those typically used for roasting are used; for example, in one embodiment coffee beans are dried at a temperature of below about 49° C. (120° F.). Suitable methods of drying can include freeze drying, belt drying, vacuum drying, oven drying, fluid bed drying, and combinations thereof. Preferably, the dried beans have a moisture content of less than about 10% in order to create a driving force for moisture absorption.

Suitable means of hydration can include treating with low pressure or atmospheric steam, spraying the coffee with the desired amount of water and allowing it to be absorbed, soaking the beans in an aqueous solution of the desired amount of water in order to create moistened beans without excess water remaining, or soaking the beans in an aqueous solution of the desired amount of water in order to create a mixture of hydrated beans and excess water (i.e., water that is not completely absorbed by the beans). Soaking the beans in excess solution is less preferred, because coffee solids may be extracted into the remaining solution, resulting in decreased flavor and lower quality beans.

In one embodiment, the beans are steamed to open up their pores in preparation for soaking in an asparagine-reducing enzyme solution. In another embodiment, the coffee beans are soaked in water and allowed to hydrate to from about 15% to about 75%, preferably from about 20% to about 55%, and more preferably from about 25% to about 40% moisture before the addition of asparagine-reducing enzyme to the solution. Hydrating the beans with aqueous solution or steam to a moisture content of greater than about 15% can cause the beans to swell and can facilitate the formation of pathways for the extraction of asparagine out of the beans, and/or for the transfer of an asparagine-reducing enzyme solution into the beans.

Subjecting a mixture of beans and excess water or asparagine-reducing enzyme solution to vacuum and/or pressure can result in more water or asparagine-reducing enzyme solution penetrating the beans and entering the beans' interior. Pressure can force the water or asparagine-reducing enzyme solution into the structure of the beans, while vacuum can pull residual air from within the beans and allow the water or asparagine-reducing enzyme solution to more readily penetrate.

Particle size reduction can create larger surface areas and can allow solution uptake and/or extraction to occur more completely, more uniformly, and more rapidly. The size of the coffee beans can be reduced by cracking, chopping, dicing, macerating, grinding, flaking, or any other suitable method. For example, cracking (such as when the bean is broken into quarter sections or smaller), or grinding (such as that performed when processing roast and ground coffee) can be used to facilitate solution uptake and/or the extraction of asparagine.

3. Adding an Asparagine-Reducing Enzyme to the Coffee Beans

As used herein, "asparagine-reducing enzyme" includes any enzyme capable of reducing the level of asparagine in coffee beans. In one embodiment, the asparagine-reducing enzyme is an enzyme capable of hydrolyzing the amide group of free asparagine. A preferred enzyme for use herein is asparaginase. A preferred source of asparaginase is Sigma-Aldrich, catalog #A2925.

As used herein, the terms "asparagine-reducing enzyme" and "enzyme" include one or more enzymes; for example, a mixture of two or more enzymes is encompassed by the terms. For example, deamidases that have asparagine-reducing functionality are included in the terms.

The enzyme may be added to the coffee beans in any suitable form. For instance, the enzyme may be added as a powder or in the form of a solution. Furthermore, the enzyme may be added to the coffee beans in any suitable manner, such as directly (for example, sprinkled, poured, or sprayed on the coffee beans, or the coffee beans can be soaked in an enzyme solution) or indirectly. As used herein, "adding" the enzyme to the coffee beans includes, but is not limited to, any means of bringing the asparagine and the enzyme together.

The enzyme may be added at any suitable stage of the method before completion of final roasting (as set forth at step 6 of the method herein) to form the roasted coffee beans. For example, the enzyme may be added to the coffee beans during or after the optional pre-treating step. Furthermore, enzyme can be added during more than one stage of the method. In one embodiment, enzyme is added to the beans post-harvest before their fruit is removed, then again after the fruit has been removed and the beans have been dried.

Enzymes are marketed by units of activity, rather than by weight or volume. Thus, the effective amount of enzyme required to achieve the desired level of acrylamide reduction will depend upon the activity of the particular enzyme product used.

The amount of enzyme to add can depend upon the level of asparagine reduction, and accordingly the level of acrylamide reduction, that is desired. The amount of enzyme to add can also depend upon the amount of asparagine present in the coffee beans; coffee beans higher in asparagine will generally require increased levels of enzyme or increased reaction time to achieve the same percentage of acrylamide reduction. The amount of enzyme to add can also depend upon the particular enzyme used (for example, the particular enzyme's enzymatic activity) and the particular type of coffee beans treated. One skilled in the art will be able to determine the effective amount of enzyme based upon the specific type of coffee, the specific enzyme, the enzyme's specific activity, and the desired result.

Preferred methods of adding the enzyme to the coffee beans include spraying, soaking, sprinkling, and dominant bath. In one embodiment, enzyme solution is applied by spraying the solution onto the beans along with gentle agitation of the beans in order to create a uniform application to all the bean surfaces.

In another embodiment, coffee beans are soaked in an enzyme solution to hydrate the beans. The amount of solution used depends upon the desired end moisture content of the beans. Enzyme solution can be used in such an amount that all the liquid is absorbed by the beans, or in such an amount that excess solution remains after solution absorption by the coffee beans. In yet another embodiment, the coffee beans are hydrated in a solution then an enzyme powder is sprinkled on the hydrated coffee beans. The beans can be removed from solution by any suitable means of separating particulates from a solution, such as by screening.

In still another embodiment, enzyme is added to the beans by means of a dominant bath. In succession, several batches of beans are soaked in an enzyme containing solution until the soluble materials that extract from the beans are in or near equilibrium with the solution. In one embodiment, the enzyme in the dominant bath converts asparagine to aspartic acid, thus creating a driving force for additional asparagine extraction on subsequent additions of batches of beans. Extractable materials can equilibrate with the beans such that additional soluble coffee components do not extract out, with the exception of asparagine, which continues to react and be converted by the enzyme. The aspartic acid that is formed from the asparagine soaks back into the beans and equilibrates. Additional water and/or enzyme-containing solution is added back after every batch of beans to make up for the solution going into the previous batch of beans; this maintains a constant volume of the dominant bath.

In one embodiment, at least a portion of the asparagine is extracted from the coffee beans, the resulting extract is treated with the enzyme, then at least a portion of the extract is added back into at least a portion of the coffee beans; for example, the enzyme may be added to the extract, or the extract may be pumped through a bed or column of immobilized enzyme (enzyme either adsorbed or chemically bonded to a substrate, preferably an inert substrate, e.g., pieces of plastic or beads in a column).

4. Allowing a Sufficient Time for the Enzyme to React with the Asparagine

The amount of time needed for the enzyme to react with the asparagine will depend upon factors including, but not limited to, the desired level of asparagine (and thus acrylamide) reduction, the characteristics of the particular coffee beans (e.g., chemical composition, amount of asparagine present, particle size), and the particular enzyme added. Preferably, the enzyme is allowed to react for a sufficient amount of time to result in coffee beans wherein the level of asparagine is reduced by at least about 10%, preferably at least about 30%, more preferably at least about 50%, still more preferably at least about 70%, and even more preferably at least about 90%. In general, the longer the enzyme is allowed to react, the greater the level of asparagine reduction and thus the greater the level of acrylamide reduction in the roasted coffee beans. The step of allowing a sufficient time for the enzyme to react can be carried out in any suitable manner; for example, it can be carried out simultaneously with adding the enzyme to the coffee beans, mixing the enzyme with the coffee beans, the absorption of the enzymatic solution by the coffee beans, or combinations thereof.

As known in the art, pH and temperature are factors that affect enzymatic activity. One skilled in the art should readily be able to determine optimal conditions of these and other parameters (e.g., water content). In addition, optimal pH and temperature conditions for specific enzymes are typically available in the literature and/or from enzyme suppliers.

Coffee beans prepared according to the method herein can have a reduction in the asparagine level of at least about 10%, preferably at least about 30%, more preferably at least about 50%, still more preferably at least about 70%, and even more preferably at least about 90%.

In one embodiment, the coffee beans comprise less than about 500 ppm asparagine, preferably less than about 300 ppm, more preferably less than about 200 ppm, and still more preferably less than about 100 ppm.

5. Optionally Deactivating or Optionally Removing the Enzyme

After the enzyme has reacted to the desired extent, it can optionally be inactivated or removed from the coffee beans. When an enzyme that is safe for consumption (e.g., naturally occurring and found in common foods) is used, one may choose not to deactivate or remove the enzyme. Alternatively, the enzyme can be deactivated by any suitable means that inactivates the enzyme. For example, the enzyme can be deactivated through the use of heat, pH adjustment, treatment with a protease, or combinations thereof. Furthermore, the enzyme can be removed from the coffee beans by any suitable means including, but not limited to, extraction. The enzyme can be deactivated, removed, or subjected to a combination of deactivation and removal.

6. Roasting the Coffee Beans to Form Roasted Coffee Beans

The coffee beans are then roasted to form roasted coffee beans. Any suitable process comprising roasting can be used. As used herein, the term "roasting" includes any suitable thermal treatment of coffee beans to create flavors that are indicative of coffee. Suitable roasting techniques can include, but are not limited to, oven roasting, extrusion roasting, steam roasting (e.g., with no post roasting), infrared roasting, microwave roasting, di-electric/induction heating roasting, and combinations thereof. Typical roasting equipment and methods for roasting coffee beans are described, for example, in Sivetz & Foote, *Coffee Processing Technology*, Avi Publishing Co., Westport, Conn., Vol. 1 (1963), pp. 203-226. The roasted coffee beans can be in any suitable form, such as decaffeinated versions, caffeinated versions, or mixtures thereof.

The coffee beans can be roasted to any desired roast color. Preferably, the beans are roasted to a Hunter color level of from about 10 L (very dark) to about 25 L (very light). As used herein, Hunter color is measured on a Hunter calorimeter from the Hunter CIE scale. See pages 985-95 of R. S. Hunter, "Photoelectric Color Difference Meter," *J. of the Optical Soc. of Amer.*, Volume 48 (1958).

Roasted coffee beans prepared according to the method herein can have a reduction in the acrylamide level of at least about 10%, preferably at least about 30%, more preferably at least about 50%, still more preferably at least about 70%, and even more preferably at least about 90%.

In one embodiment, the roasted coffee beans comprise less than about 160 ppb acrylamide, preferably less than about 150 ppb acrylamide. In another embodiment, the roasted coffee beans comprise less than about 135 ppb acrylamide, preferably less than about 120 ppb, more preferably less than about 100 ppb, still more preferably less than about 50 ppb, even more preferably less than about 20 ppb, and most preferably less than about 10 ppb.

The roasted coffee beans can be used as is or can be used to make a variety of roasted coffee products, such as roast and ground coffees, liquid concentrates, instant or powdered coffees, coffee beverages (e.g., hot and cold ready to serve coffees, vended coffees, commercial and at-home brewed coffees, Kahlua™, lattes, cappuccinos), mixes (e.g., café latte mixes), confectionaries (e.g., candy), desserts (e.g., cakes, ice creams, mousses, custards), pastries (e.g., danish, donuts), sauces, and soups (e.g., chili). In one embodiment, the coffee beans are dried, roasted, then ground to form roast and ground coffee. Typical grinding equipment is described, for example in Sivetz & Foote, supra, pp. 239-250.

Roasted coffee products comprising the roasted coffee beans of the present invention can have a reduction in the acrylamide level of at least about 10%, preferably at least about 30%, more preferably at least about 50%, still more preferably at least about 70%, and even more preferably at least about 90%. In one embodiment, roast and ground coffee comprises less than about 160 ppb acrylamide, preferably less than about 150 ppb. In another embodiment, roast and ground coffee comprises less than about 135 ppb acrylamide, preferably less than about 120 ppb, more preferably less than about 100 ppb, still more preferably less than about 50 ppb, even more preferably less than about 20 ppb, and most preferably less than about 10 ppb. In another embodiment, a roast and ground coffee brew comprises less than about 7 ppb acrylamide, preferably less than about 5 ppb acrylamide.

Deactivating the enzyme may occur through heating, thus the optional deactivation step and roasting the coffee beans may be carried out simultaneously. Heat processing can denature and inactivate the enzyme such that the roasted coffee beans are not subjected to continuing enzymatic activity. Furthermore, at least a portion of the time allowed for enzymatic reaction may be carried out during the roasting step.

B. Means of Practicing the Method

The present invention can be practiced by any suitable means. For example, the method herein can be practiced in batch, semi-batch, or continuous mode.

C. Preferred Embodiments

Although the method herein will generally be described in terms of preferred embodiments set forth below, it should be understood by one skilled in the art that the method herein can be practiced in any suitable manner.

In one embodiment coffee beans are dried to a moisture content of less than about 15%, preferably less than about 10%, more preferably less than about 5%, and most preferably from about 1.5% to about 4%. For example, the beans can be dried at 49° C. (120° F.) overnight. Drying increases the potential for the beans to absorb more enzymatic solution. Optionally, the beans can be cracked or ground. The beans are then put into a solution comprising enzyme and allowed to soak. The enzyme is allowed to react for from about 45 minutes to about 1 hour at a temperature of about 38° C. (100° F.); then, optionally the enzyme is deactivated by microwaving. The beans are then dried to a moisture content of from about 7% to about 11% at 74° C. (165° F.). The beans are then roasted to a roast color of from about 16 L to about 24 L on a Probat Duett™ roaster, then ground to form roast and ground coffee.

In yet another embodiment, a dominant bath is employed. Coffee beans are optionally pre-wet with steam to a moisture content of from about 15% to about 30%. They are then soaked in excess water to create a dominant bath (i.e., not all the water is taken in by the beans). The beans are then separated from the water, such as by screening them out of the solution. This procedure is repeated several times to form a dominant bath. In the dominant bath, an equilibrium can be established between the water soluble components that are in the beans and in the bath. Enzyme is then added to the bath. The enzyme selectively converts the asparagine to aspartic acid. New beans are then added to the enzyme-containing dominant bath. Asparagine extracts out of the beans into the dominant bath and the enzyme converts the asparagine to aspartic acid. The excess aspartic acid in the bath establishes equilibrium with the beans. Thus, the net effect is the conversion from asparagine to aspartic acid. The beans are removed from the dominant bath. Additional batches of beans can be processed in a continuous or semi-continuous fashion. The beans can then be processed in the typical manner known in the art, such as by drying, roasting, then grinding to form roast and ground coffee.

D. Article of Commerce

In another aspect, the present invention provides an article of commerce. In one embodiment, the article of commerce comprises:

(a) a product comprising roasted coffee beans, wherein said roasted coffee beans have a reduced level of acrylamide;
(b) a container for containing the product; and
(c) a message associated with the container.

The message associated with the container informs the consumer that the roasted coffee beans, the product comprising the roasted coffee beans, and/or the article of commerce has a reduced level of acrylamide. In one embodiment, the message informs the consumer that the roasted coffee beans, the product comprising roasted coffee beans, and/or the article of commerce is made with coffee beans having reduced or low levels of asparagine. The message can be printed material attached directly or indirectly to the container, attached directly or indirectly near the container, or alternatively can be a printed, electronic, or broadcast message associated with the container. Suitable messages include, but are not limited to, messages that communicate "reduced" or "low" levels of acrylamide, messages that communicate that less than a specified amount of acrylamide is present, and messages that communicate that the roasted coffee beans, product comprising roasted coffee beans, and/or article of commerce meet or exceed a suggested or mandatory level (e.g., regulatory threshold or signal level).

In another embodiment, the article of commerce comprises:

(a) a product comprising coffee beans, wherein said coffee beans have a reduced level of asparagine;
(b) a container for containing the coffee beans; and
(c) a message associated with the container.

The message associated with the container informs the consumer that the coffee beans, the product comprising the coffee beans, and/or the article of commerce has a reduced level of asparagine. The message can be printed material attached directly or indirectly to the container, attached directly or indirectly near the container, or alternatively can be a printed, electronic, or broadcast message associated with the container. Suitable messages include, but are not limited to, messages that communicate "reduced" or "low" levels of asparagine, messages that communicate that less than a specified amount of asparagine is present, and messages that communicate that the coffee beans, product comprising coffee beans, and/or article of commerce meet or exceed a suggested or mandatory level (e.g., regulatory threshold or signal level).

Any container from which the product comprising the roasted coffee beans or coffee beans can be dispensed, presented, displayed, or stored is suitable. Suitable containers include, but are not limited to, bags, canisters, boxes, bowls, plates, tubs, and cans.

Analytical Methods

Parameters used to characterize elements of the present invention are quantified by particular analytical methods. These methods are described in detail as follows.

1. Acrylamide

Method for Measuring Acrylamide (AA) in Food Products

Summary

Roast and ground coffee is spiked with $^{13}$C-AA and extracted with hot water. The aqueous supernatant is extracted twice with ethyl acetate, and the ethyl acetate extracts are concentrated and analyzed by LC/MS with selected ion monitoring for specific detection of AA and $^{13}$C-AA.

Extraction of Ground Coffee Beans (Both Green and Roasted)

1. Weigh 6.00±0.01 g of sample into a 125-mL Erlenmeyer flask.
2. Add 120 μL of 100 ng/μL $^{13}$C-AA in de-ionized distilled water (ISTD 2), with an adjustable 1000-μL pipette (calibrated), directly onto the sample.
3. Using a dispenser, add 40 mL of de-ionized distilled water to the flask and cover with foil.
4. Place into a 65° C. water bath for 30 min.
5. With a dispenser, add 10 mL of ethylene dichloride to the flask, and homogenize with a Tekmar Tissumizer™ (SDT-1810) or an Ultra Turrax® (T18 Basic) for 30 seconds. Rinse the dispersing element into the flask with deionized distilled water.
6. Place 25 g of the homogenate into an 8-dram vial
7. Tightly cap the vial and centrifuge for 30 minutes at 2500-5200 RPM.
8. Condition a Sep-Pak® Plus C18 (Waters #WAT020515) with 3 mL acetonitrile followed by 6 mL of deionized distilled water.
9. Pass 6 mL of the supernatant through the cartridge and elute into an 8-dram vial.
10. Add 10 mL of ethyl acetate to the vial with a dispenser, cap, and vortex for 10 seconds.
11. Allow any emulsion to break up; help by swirling or shaking once or twice and then allowing layers to split.
12. Transfer as much of the top layer as possible to a scintillation vial, without transferring any liquid from the interface. Extract once more with a 10-mL portion of ethyl acetate and add to the same scintillation vial. Then, add approximately 2 g of anhydrous sodium sulfate.
13. Concentrate the extract with a gentle stream of nitrogen in a 60-65° C. water bath to about 1 mL. Transfer the extract to a Pierce REACTI-VIAL™ (or equivalent conical shaped glass vial) and further concentrate the extract to a final volume of approximately 100-200 μL. Place this extract into an autosampler vial with a conical sleeve and cap.

Preparation of Standards

Stock Solutions and Internal Standards

| Solution | Weight | Volumetric Flask (mL) | Solvent | Concentration (ppm) |
| --- | --- | --- | --- | --- |
| Stock 1 | 0.1000 g Acrylamide (AA) | 100 | Ethyl Acetate | 1000 |
| ISTD 1 | 0.0100 g $^{13}$C-Acrylamide | 100 | Ethyl Acetate | 100 |
| Stock 2 | 0.1000 g Acrylamide (AA) | 100 | Deionized Distilled Water | 1000 |
| ISTD 2 | 0.0100 g $^{13}$C-Acrylamide | 100 | Deionized Distilled Water | 100 |

Intermediate Standards

| Solution | Volume Stock 1 AA (μL) | Volumetric Flask (mL) | Solvent | Concentration (ppm) |
| --- | --- | --- | --- | --- |
| INT 1 | 100 | 10 | Ethyl Acetate | 10 |
| INT 2 | 1000 | 10 | Ethyl Acetate | 100 |

Calibration Standards

| Standard | Volume INT 1 (μL) | Volume INT 2 (μL) | Volume ISTD 1 (μL) | Volumetric Flask (mL) | Solvent | Conc. AA (ppm) | Conc. ISTD 1 (ppm) |
| --- | --- | --- | --- | --- | --- | --- | --- |
| 0 | 0 | 0 | 450 | 10 | Ethyl Acetate | 0 | 4.50 |
| 0.25 | 250 | 0 | 450 | 10 | Ethyl Acetate | 0.250 | 4.50 |
| 0.75 | 750 | 0 | 450 | 10 | Ethyl Acetate | 0.750 | 4.50 |
| 1.5 | 0 | 150 | 450 | 10 | Ethyl Acetate | 1.50 | 4.50 |
| 3.0 | 0 | 300 | 450 | 10 | Ethyl Acetate | 3.00 | 4.50 |
| 5.0 | 0 | 500 | 450 | 10 | Ethyl Acetate | 5.00 | 4.50 |

Homogenizer Cleaning Procedure

Use this cleaning procedure between every sample.
1. Fill a 1-L Erlenmeyer flask with hot tap water (≈80% full) and add a drop of Dawn™ dishwashing liquid (available from the Procter & Gamble Co.) or equivalent.
2. Insert the homogenizer dispersing element into the water as far as possible.
3. Homogenize the solution for about 10-15 seconds.
4. Empty the cleaning solution from the Erlenmeyer; rinse and refill the flask with hot tap water.
5. Homogenize again for about 10-15 seconds.
6. Empty the flask and refill with hot tap water; homogenize again for about 10-15 seconds.
7. If the water is not clear and free of particulates, continue homogenizing clean hot tap water as many times as necessary to achieve this condition.
8. When the hot tap water is clear and free of particulates, rinse the dispersing element with deionized distilled water.

Analysis by LC/MS

Samples are analyzed using a Waters 2690 LC interfaced to a Micromass LCZ mass spectrometer.

| | |
| --- | --- |
| Mobile Phase | 100% $H_2O$, 10 mM $NH_4Ac$, adjusted to pH 4.6 w/ formic acid |
| Column | 2.0 mm × 150 mm, YMC C18 AQ-3 μm, 120 Å (available from Waters Corp.) |
| Flow rate | 0.2 mL/min |
| Interface | Direct (no split) |
| Injection volume | 5 μL |
| MS ionization mode | Electrospray, positive ion mode |

| | |
|---|---|
| MS detection mode | Selected ion monitoring: m/z 72 (AA), m/z 73 ($^{13}$C-AA); dwell times: 0.5 s |

Data Analysis

Response ratios (area of AA peak/area of $^{13}$C-AA peak) are plotted against the corresponding concentration ratios for a series of six standards in ethyl acetate. All standards contain 4.50 μg/mL $^{13}$C-AA, and AA concentrations ranging from 0 to 5.0 ppm. Linear regression results in a calibration curve from which concentration ratios in extracts are determined from measured response ratios. When this concentration ratio is multiplied by the accurately known $^{13}$C-AA level (nominally 2 ppm) added to sample in step three of the extraction procedure, the level of AA in ppm results.

Sample Calculation for LC/MS:

The calibration curve is generated by plotting the response ratio (area mz/72/area m/z 73) on the y axis vs. the concentration ratio ([acrylamide]/[13 C-acrylamide]) on the x axis. For this example, the equation of that line is y=0.899x+ 0.0123.
Measured area of AA peak (m/z 72) at 4.0 min: 100,000
Measured area of 13C-AA peak (m/z 73) at 4.0 min: 500,000
Response ratio $R_r$=0.200. From the slope and intercept of the calibration curve, the concentration ratio $R_c$ is calculated: $R_c$=(0.200−0.0123)/0.899=0.209
Given the spike level of 13C-AA in the sample (2 ppm), the measured level of AA is 0.209×2 ppm=0.418 ppm Quality Assurance/Quality Control (QA/QC)
1. All balances used in the preparation of standards and/or samples, must have their calibrations checked weekly with a set of qualified weights. The balances should be checked with at least three weights covering the range of sample/standard weights to be measured.
2. A six-point calibration curve should be performed daily.
3. A working reference material (WRM) should be analyzed with each set of samples. The concentration of this material should be within 2 σ of the running mean. If it is not, the instrument should be recalibrated and the WRM recalculated.

2. Asparagine

Determination of Asparagine and Aspartic Acid in Food and Beverage Products

Principle

A weighed amount of sample is mixed with 5% HCl and heated for 30 minutes, then homogenized. A portion of the homogenate is centrifuged and then a portion of the supernatant is diluted and treated with FMOC reagent (9-fluorenylmethyl chloroformate), which reacts with asparagine and aspartic acid to form a highly fluorescent derivative. Reverse-phase HPLC is then used to resolve FMOC-asparagine from other sample matrix components. Detection is by fluorescence emission at 313 nanometers (nm) upon excitation at 260 nm. Analysis of standards of known concentration permits quantification.

LINEARITY

Working calibration curve of four standards (50-600 ppm) give a correlation of 0.998 or better. A curve taken out to 2000 ppm also gives a correlation of 0.998.

Accuracy

Coffee samples:
A roast and ground coffee sample is spiked at four levels of both asparagine and aspartic acid (40, 200, 400, and 600 ppm). Asparagine is recovered at 86% (Relative standard deviation of less than 4%) and aspartic acid is recovered at 92% (Relative standard deviation of less than 4%).

REFERENCES
1. Herbert, P.; Santos, L; Alves, A. Journal of Food Science (2001), 66(9), 1319-1325.
2. Heems, Dany; Luck, Geneviewe; Fraudeau, Chrisophe; Verette, Eric. Journal of Chromatography, A (1998), 798 (1+2), 9-17.

Below are Suggested Chemicals and Equipment; However, Substitutions of Equivalent Materials are Acceptable.

Chemicals
Water, HPLC or Milli-Q™ Grade (Millipore)
Acetonitrile, HPLC Grade Burdick & Jackson #AH015-4
Methanol, HPLC Grade Fisher #A452-4
Ethyl Acetate Baker #9280-3
Pentane Burdick & Jackson #GC312-4
Asparagine monohydrate EM Science
Aspartic acid Sigma #A-8949
aminoisobutyric acid Sigma #A-8379
9-Fluorenyl Chloroformate (FMOC) ICN #150200
Sodium Borate EM Science #SX 0355-1
Boric Acid Fisher #A-73
Sodium Bicarbonate ICN #194847
Tetramethyl Ammonium Chloride Fisher #04640-500
Sodium Citrate anhydrous MCB #SX445
Citric Acid Baker #0122-01
Acetone Burdick & Jackson #010-4
Hydrochloric Acid, 0.1N Fisher #SA48-500
Calcium Chloride Dihydrate Aldrich #22,350-6

Equipment
Transfer Pipettes, polyethylene (Samco #222)
Volumetric Flasks (25, 100, 250, 1000 ml)
Volumetric Pipet (10 ml)
Graduated Cylinders (100-1000 ml)
HPLC reservoirs (500 ml, 1 or 2 liter)
Beakers
Magnetic stirrers/stir bars
Analytical (4-place) balance
Scintillation Vials
Centrifuge tubes, screw cap (100×16 mm) with caps
Autosampler vials (8×30 mm, 1 ml), with crimp caps Safety:
This method requires the use of a fume hood, and involves exposure to chemicals. Please review Safe Practices for Fume Hood Use and Chemical Spills.

| INSTRUMENT | MODEL | MANUFACTURER |
|---|---|---|
| Robot | Microlab ® SPE | Hamilton |
| Pump/HPLC injector | HP 1100 | Agilent |
| Detector | RF10AXL | Shimadzu |
| Data System | Chemstation | Agilent |

Column

Phenomenex Luna 100×4.6 mm C-18(2) 3 micron #00D-4251-EO

Preparation of Reagents

Diluent (pH 8.3-8.5; 1000 ml).
1. Weigh 3.0 grams of Sodium Borate, 3.0 grams of Boric Acid, and 8.0 grams of Sodium Bicarbonate into a dry tared beaker.
2. Place an empty 800 ml beaker on a magnetic stirrer. Add about 500 ml of Milli-Q™ water and a stir bar. Stir the water vigorously without splashing.
3. Quantitatively transfer the reagents from step 1 to the water; stir until they are completely dissolved.
4. Quantitatively transfer the solution from step 3 to a 1-liter volumetric flask and dilute to volume with Milli-Q™ water; mix well. Stable for up to six (6) months.

Calcium Chloride Solution (100 grams).
1. Weigh 40 grams of Calcium Chloride Dihydrate into a tared 250 ml beaker.
2. Add 60 grams of Milli-Q™ water. Mix well. Store at ambient conditions in a capped glass bottle. Stable for up to 1 year.

Extraction Solvent (Pentane: Ethyl Acetate 80:20; 500 ml)

Safety:
pentane and ethyl acetate are volatile and flammable. Perform the following operations in a Fume Hood.
1. Transfer 400 ml of pentane to a 500 ml HPLC reservoir bottle.
2. Add 100 ml ethyl acetate. Mix well. Store capped in/under the Fume Hood.

Mobile Phase (Buffer:Methanol:Acetonitrile 60:5:35,pH 3.2, 2 L)
1. Weigh 1.35 grams of Tetramethyl Ammonium Chloride, 3.65 grams of Citric Acid, and 1.60 grams of Sodium Citrate into a dry tared beaker.
2. Place an empty 800 ml beaker on a magnetic stirrer. Add about 500 ml of Milli-Q™ water and a stir bar. Stir the water vigorously without splashing.
3. Quantitatively transfer the reagents from step 1 to the water; stir until they are completely dissolved.
4. Quantitatively transfer the solution from step 3 to a 1 liter graduated cylinder and dilute to 1000 ml with Milli-Q™ water; mix well.
5. Transfer to a 2-liter HPLC mobile phase reservoir.
6. Add 200 ml Milli-Q™ water, 100 ml methanol and 700 ml acetonitrile. Add the latter two solvents slowly with vigorous stirring. Perform this operation in a hood, and wear personal protective equipment. Refer to the relevant Material Safety Data Sheets (MSDS) for specific details.
7. Degas the mobile phase by vacuum aspiration while stirring.

FMOC Reagent Solution (in Acetone)
1. Weigh 0.10 grams of FMOC reagent into a tared 100 ml volumetric flask.
2. Add acetone to dissolve and dilute to volume with same. Mix well. Perform this operation in a hood. Wear PPE specified in the MSDS for the chemicals.
3. Store refrigerated for no more than six (6) months.

Acid Solution for Sample Extraction (5% HCl)
1. Add 100 ml of Milli-Q™ water into a 200 ml volumetric.
2. Add 4 ml of 1N HCl to volumetric.

Bring to volume with Milli-Q™ water.

Preparation of Internal Standard (Aminoisobutyric Acid)

ISTD A—Internal Standard StockA
1. Weigh 0.5 grams of aminoisobutyric acid into a tared 250 ml volumetric
2. Add 25 ml of 1.0N HCl and about 100 ml Milli-Q™ water. Mix by swirling until dissolved.

Dilute to volume with Milli-Q™ water and mix well. Store refrigerated for no more than six (6) months.

ISTD B—Working Internal Standard Solution B (this Solution is Added to Calibration Standards)
1. Pipet 1 ml of Internal Standard Stock A into a 100 ml volumetric flask.
2. Dilute to volume with Milli-Q™ water. Stable for one month.

Preparation of Calibration Standard(s)

Stock Calibration Solution.

Into a tared 50 ml volumetric, weigh 0.100 g (+/−0.001 g) asparagine and 0.100 g (+/−0.001 g) aspartic acid. Add 25 mL Milli-Q™ water and 1 mL 1N HCl. Place in sonic bath until dissolved, then bring to volume with Milli-Q™ H2O. Solution is good for 6 months refrigerated.

Working Standards.

Prepare the following working calibration standards:

| Std # | mL stock | final volume (mL) | ppm |
|---|---|---|---|
| 1 | 5 | 200 | 50 |
| 2 | 5 | 100 | 100 |
| 3 | 1 | 10 | 200 |
| 4 | 3 | 10 | 600 |

Solutions good for one month refrigerated.

Preparation of Samples
1. Weigh 6 grams of ground coffee* into 125 ml Erlenmeyer flask.
2. Add 48.0 ml of 5% HCl solution to each sample.
3. Add 2 ml ISTD A to each sample.
4. Cover each flask with aluminum foil and place in 60 C water bath for 30 minutes.
5. Add 10 mL dicloroethane to each sample.
6. Homogenize sample for 60 seconds.
7. Pour portion of sample into 30 ml centrifuge tube.
8. Centrifuge at 10000 rpm for 32 minutes at 5 C. The supernatant is used in "Samples—Diluting" step 1.

*If coffee samples are not finely ground, grind in small food processor before weighing. If samples are high in moisture, add several pieces of dry ice while grinding.

Preparation of Standards and Samples

Three Microlab methods are run in order to dilute the samples/standards, add the internal standard, and form the FMOC derivative. These are summarized below.

| Operation | Microlab ® method used |
|---|---|
| Dilution | TRANSDIL |
| Addition of Internal Standard | ADDISTD |
| Formation of FMOC derivative | ADDFMOC |

Preparation of Samples and Standards Using Microlab® Robot

Step 1: Standards—Adding ISTD and Dilution Step
1. Prepare two sets of tubes for each standard. Place approximately 2 mL of standard in one set of tubes place these filled tubes on the left most position of the Microlab®.
2. Place the rack with empty tubes in the rightmost rack position of the Microlab®.
3. Fill a 20 ml glass (scintillation) vial with Working Internal Standard Solution B and place on the Microlab® workspace.
4. Select method ADDISTD. (Mixes 200 ul ISTD B, 50 ul standard solution, to 4000 ul total volume with Milli-Q™ water).
5. Execute the method.
6. Remove the tube set from the left position and set aside for discard.
7. Remove the Working Internal Standard Solution from the Microlab® work space and refrigerate.

Set aside right side tubes for step 3.

Step 2: Samples—Dilution Step (ISTD was Already Added during Sample Preparation)
1. Prepare two sets of tubes for each sample. Place approx. 2 mL of sample in one set of tubes, place these filled tubes on the left most position of the Microlab®.
2. Place the rack with the empty tubes in the rightmost rack position of the Microlab®.
3. Select method TRANSDIL. (Set # of samples, 50 ul for amount of sample, and 4000 ul for final dilution amount with Milli-Q™ water.)
4. Execute the method.
5. Remove the tube set from the left position and set aside for discard.

Set aside right side tubes for step 3.

Step 3: Addition of FMOC Reagent—Making Fluorescent Derivative
1. Prepare a rack of 100×16 mm screw-cap tubes.
2. Place the rack in the rightmost rack position of the Microlab®.
3. Place standard and sample tubes from above dilution steps in leftmost rack position of Microlab®.
4. Transfer an aliquot (22 mL) of FMOC reagent solution to a glass scintillation vial. Add approximately 100 μL of 40% Calcium Chloride solution; mix well. (Calcium chloride is added to make the FMOC reagent "charged"—necessary for detection by Microlab®).
5. Place the vial on the Microlab® workspace.
6. Select method ADDFMOC.
7. Switch syringes 1 & 2 from water to Diluent (pH 8.3–8.5).
8. Perform a wash of at least five (5) cycles for syringes 1 & 2 using Diluent (pH 8.3–8.5)
9. Execute method ADDFMOC. (mixes 450 ul of FMOC solution, 250 ul sample from ADDISTD above to final volume of 1300 ul with diluent solution).
10. Remove the tube set from the SAMPLE rack position and set aside.
11. Remove the FMOC reagent solution from the Microlab® workspace and refrigerate.
13. Remove the tube set from the rightmost position and place in fume hood. Let stand for at least 10 minutes or until solution is clarified (but no longer than 20 minutes).
14. Add 2 ml of Extraction Solvent to each tube. Cap and vortex at high speed for two (2) minutes to extract unreacted FMOC reagent.
15. Prepare another tube set of 55×16 mm tubes. Add 1 ml of mobile phase solution to each tube.
16. Transfer the 1.0 mL of aqueous (lower) layer from the centrifuge tubes to the 55×16 mm tubes.
17. Discard the upper (organic) layer.
18. Transfer samples to autosampler vials and seal.

Chromatography

Operating Conditions

HP 1100 with Chem Station Software

Detector: Waters 474 Scanning Fluorescence Detector
  Mode: Norm
  Signal: 0.0000
  Wavelength: Ex 260
    Em 313
  Gain: 10
  Atten: 1
  Response: FST
Column: Phenomex Luna C18 (2) 100×4.6 mm 3 u LC Method Flow: 1.000 ml/min
Isocratic run (see preparation of reagents—Mobile Phase)
Injection volume: 10.0 ul
Temperature settings: not controlled Calculations Sample solutions are calculated against a standard curve of known amounts using-area counts:

$$y = mx + b$$

$$y(\text{ratio asparagine/ISTD}) = m(\text{slope}) \times (\text{asparagine concentration}) + b(\text{y-intercept})$$

$$(y-b)/m = x$$

ppm asparagine = (area aspargine/area ISTD − intercept)/slope

[ppm = ug/mL]

Example:

$$\text{ppm asparagine} = (215.45436/551.828 - -0.0165)/0.0023 = 176.93 \text{ ppm}$$

Correction for dilution/homogenization in sample preparation step.

$$\text{ug/g aspargine} = \text{ppm aspargine found} \times \frac{\text{mL sample dilution}(50)}{\text{grams of sample}}$$

[ppm=ug/mL]

Example:

$$\text{ug/g aspargine} = 176.93 \text{ ppm} \times \frac{50 \text{ mls}}{1.0083 \text{ g}} = 8773.65 \text{ ug/g}$$

Run Acceptability Criteria:
  the Check Sample of Working Reference Material accuracy must be within 10% of known result for asparagine.
  the linearity of the calibration curve ($r^2$) must be 0.995 or greater.

Sample Chromatogram of LC Analysis

Figure 3:
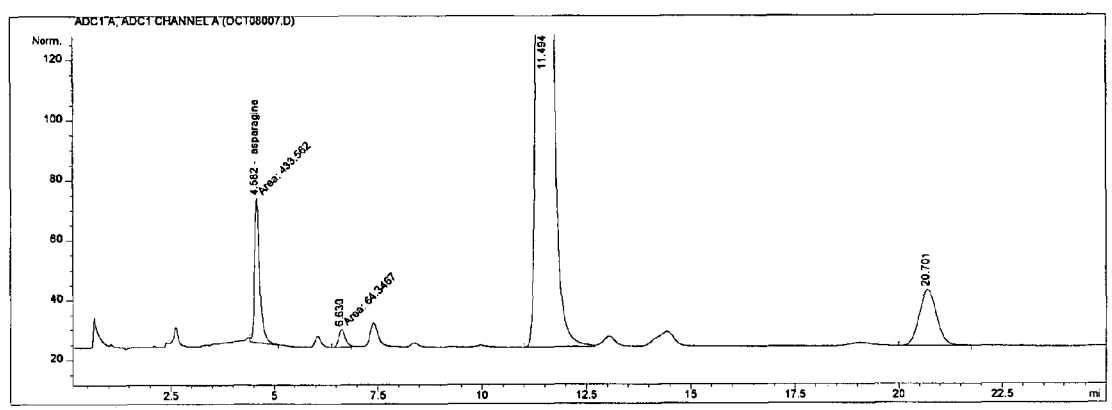
FIG. 3.

FIG. 3 sets forth a sample chromatogram of LC analysis.

| RT | Compound |
|---|---|
| 4.5 min | Asparagine |
| 6.6 min | aspartic acid |
| 11.5 min | FMOC reagent |
| 20.7 min | ISTD |

3. % Reduction of Acrylamide

% Reduction Acrylamide=[(Acrylamide level in control sample−Acrylamide level in enzyme-treated sample)/Acrylamide level in control sample]×100.

The control sample is prepared in the conventional manner as known in the art. Both the control and the enzyme-treated sample are roasted in the same manner and to about the same Hunter L color.

4. % Reduction of Asparagine

% Reduction Asparagine=[(Asparagine level in control sample−Asparagine level in enzyme-treated sample)/Asparagine level in control sample]×100.

The control sample is prepared in the conventional manner as known in the art. If roasted, both the control and the enzyme-treated sample are roasted in the same manner and to about the same Hunter L color.

EXAMPLES

The following examples are illustrative of the present invention but are not meant to be limiting thereof.

Example 1

Enzyme Solution Absorption

An enzyme solution is formulated consisting of 1,000 units of Asparaginase and 0.1% (of coffee weight) of a cellulase dissolved in 600 grams of distilled water. Twelve hundred grams of washed *arabica* green coffee beans from Guatemala are placed in a 3 liter round bottom flask, which is then placed on a rotovap with a water bath set at 35° C. A 25 inch vacuum is pulled on the rotating flask for 5 minutes, then enough enzyme solution is added to the flask to wet the surface of the coffee beans. The vacuum is then released. The vacuum is applied to the system for about 10 seconds and then released 2 more times. The flask of coffee beans is then left to rotate at atmospheric pressure until all of the enzyme solution on the surface of the beans is absorbed. This process is repeated until 600 grams of enzyme solution is added to the coffee.

The coffee is then transferred to a pressure vessel and 80 psi pressure is applied using nitrogen gas. The wet coffee is kept under pressure for 2 hours, with samples being removed at 1 and 2 hours. The enzyme is deactivated by microwave heating. The samples are then dried at 50-60° C. and roasted to a roast color of about 17 L. Optionally, the samples are then ground to form roast and ground coffee.

| Enzyme-Treated Samples | Asparagine (green)* | Acrylamide (roasted) |
|---|---|---|
| 1 hour of pressure | 384 ppm | 346 ppb |
| 2 hours of pressure | 393 ppm | 280 ppb |

*Asparagine values are reported on a 0% moisture basis.

For calculation of the percent reduction of asparagine and acrylamide, the asparagine and acrylamide values for coffee beans that have not been treated with asparaginase solution are measured. The asparagine value is 661 ppm (on a 0% moisture-basis), and the acrylamide value is 397 ppb. The percent reduction of both asparagine and acrylamide are set forth in the table below.

| Enzyme-Treated Samples | % Asparagine Reduction | % Acrylamide Reduction |
|---|---|---|
| 1 hour of pressure | 42 | 13 |
| 2 hours of pressure | 40 | 29 |

Example 2

Dominant Bath

Washed *arabica* green coffee beans (Sample #1, Green) are moistened to about 25% moisture using atmospheric pressure steam. The coffee beans are then soaked in water in a ratio of steamed coffee beans to water of about 1:4 with gentle agitation for about 30 minutes. The extracted coffee beans are removed and the extract is then used to soak another batch of pre-moistened coffee beans. This process is repeated, with a coffee beans to extract ratio of between about 1:4 and about 1:1, until the solids contained in the extract achieve a constant level.

This extract is used to soak a fresh batch of pre-moistened green coffee beans in a ratio of 270 g pre-moistened coffee to 504 g of extract for 20 minutes with gentle agitation. The coffee beans are separated from the extract (this extract is Sample #2), dried (these dried beans are Sample #3 Green), and roasted (these dried and roasted beans are Sample #3 Roasted). The roasted coffee beans are then optionally ground to form roast and ground coffee.

300 units of asparaginase is added to 350 grams of extract and is allowed to sit for 1 hour to allow the asparaginase to convert the asparagine to aspartic acid (the enzyme-treated extract is Sample #4). The extract is then used to soak another fresh batch of pre-moistened *arabica* green coffee beans for 1 hour in a ratio of coffee beans to extract of about 0.8:1. The coffee beans are separated from the extract, the enzyme is de-activated, and the beans are dried (these dried beans are Sample #5 Green) and roasted (these dried and roasted beans are Sample #5 Roasted). The beans are roasted to a roast color of about 17 L. The roasted coffee beans are then optionally ground to form roast and ground coffee. An aliquot of Sample #1, Green, is roasted to form Sample #1, Roasted.

Analytical measurements of coffee beans that are soaked in the enzyme-treated extract show the following levels of asparagine and acrylamide:

| Sample | Asparagine (Green)* | Acrylamide (Roasted) |
| --- | --- | --- |
| Sample #1, Control Coffee Beans | 661 ppm | 397 ppb |
| Sample #2, Extract Before Enzymatic Treatment | 385 ppm | N/A** |
| Sample #3, Beans Soaked in Sample #2 | 436 ppm | 399 ppb |
| Sample #4, Extract After Enzymatic Treatment | 8 ppm | N/A** |
| Sample #5, Beans Soaked in Sample #4 | 240 ppm | 291 ppb |

*Asparagine values are reported on a 0% moisture basis.
**Not applicable

The percent reduction of both asparagine and acrylamide for coffee beans and extracts are set forth in the table below.

| Sample | % Asparagine Reduction | % Acrylamide Reduction |
| --- | --- | --- |
| Sample #5 (compared versus Sample #1) | 64% | 27% |
| Sample #4 (compared versus Sample #2) | 98% | N/A* |

*Not applicable

Example 3

Dominant Bath with Deactivated Enzyme

Washed *arabica* green coffee beans (Sample #1, Green) are moistened to about 25% moisture using atmospheric pressure steam. The coffee beans are then soaked in water in a ratio of steamed coffee beans to water of about 1:4 with gentle agitation for about 30 minutes. The extracted coffee beans are removed and the extract is then used to soak another batch of pre-moistened coffee beans. This process is repeated, with a coffee beans to extract ratio of between about 1:4 and about 1:1, until the solids contained in the extract achieve a constant level.

This extract is used to soak a fresh batch of pre-moistened green coffee beans in a ratio of 270 g pre-moistened coffee to 504 g of extract for 20 minutes with gentle agitation. The coffee beans are separated from the extract (this extract is Sample #2), dried (these dried beans are Sample #3 Green), and roasted. The roasted coffee beans are then optionally ground to form roast and ground coffee.

300 units of asparaginase is added to 350 grams of extract and is allowed to sit for 1 hour to allow the asparaginase to convert the asparagine to aspartic acid. The enzyme treated extract is then deactivated (the enzyme-treated, deactivated extract is Sample #4). The extract is then used to soak more pre-moistened *arabica* green coffee beans for 1 hour in a ratio of coffee beans to extract of about 0.8:1. The coffee beans are separated from the extract. The beans are dried (these dried beans are Sample #5 Green) and roasted. The roasted coffee beans are then optionally ground to form roast and ground coffee.

Analytical measurements of coffee beans that are soaked in the enzyme-treated extract show the following levels of asparagine:

| Sample | Asparagine (Green) |
| --- | --- |
| Sample #1, Control Coffee Beans | 661 ppm |
| Sample #2, Extract Before Enzymatic Treatment | 385 ppm |
| Sample #3, Beans Soaked in Sample #2 | 436 ppm |
| Sample #4, Extract After Enzymatic Treatment (deactivated) | 7 ppm |
| Sample #5, Beans Soaked in Sample #4 | 320 ppm |

The percent reduction of asparagine for coffee beans and extracts are set forth in the table below.

| Sample | % Asparagine Reduction |
| --- | --- |
| Sample #5 (compared versus Sample #1) | 52 |
| Sample #4 (compared versus Sample #2) | 98 |

The level of acrylamide in the enzyme-treated roasted coffee beans, the roast and ground coffee, and coffee brews prepared therefrom is reduced by at least about 10% compared to conventionally processed products.

Example 4

Dominant Bath with Immobilized Enzyme

Washed *arabica* green coffee beans (Sample #1, Green) are moistened to about 25% moisture using atmospheric pressure steam. The coffee beans are then soaked in water in a ratio of steamed coffee beans to water of about 1:4 with gentle agitation for about 30 minutes. The extracted coffee beans are removed and the extract is then used to soak another batch of pre-moistened coffee beans. This process is repeated, with a coffee beans to extract ratio of between about 1:4 and about 1:1, until the solids contained in the extract achieve a constant level.

This extract is used to soak a fresh batch of pre-moistened green coffee beans in a ratio of 270 g pre-moistened coffee to 504 g of extract for 20 minutes with gentle agitation. The coffee beans are separated from the extract (this extract is Sample #2), dried (these dried beans are Sample #3 Green), and roasted (these dried and roasted beans are Sample #3 Roasted). The roasted coffee beans are then optionally ground to form roast and ground coffee.

The extract is contacted with immobilized asparaginase (this enzyme-treated extract is Sample #4). The extract is then used to soak more pre-moistened *arabica* green coffee beans for 1 hour in a ratio of coffee beans to extract of about 0.8:1. The coffee beans are separated from the extract, then the beans are dried (these dried beans are Sample #5 Green) and roasted (these dried and roasted beans are Sample #5 Roasted). The roasted coffee beans are then optionally ground to form roast and ground coffee. An aliquot of Sample #1, Green, is roasted to form Sample #1, Roasted. The level of acrylamide in the enzyme-treated roasted coffee beans, the roast and ground coffee, and coffee brews prepared therefrom is reduced by at least about 10% compared to conventionally processed products.

Example 5

Decaffeinated Roast and Ground Coffee

The dried enzyme-treated (2 hour pressure) green *arabica* coffee beans from Example 1 are taken prior to roasting and subjected to a decaffeination process. The decaffeination process as outlined in U.S. Pat. No. 4,474,821 to Morrison, Jr. et al. is followed to decaffeinate the beans to a point where 97% of the original caffeine level in the beans has been extracted. The beans are then roasted and ground to produce a decaffeinated roast and ground coffee having at least about 10% acrylamide reduction compared to conventionally processed products.

Example 6

Decaffeinated Roast and Ground Coffee

Green *arabica* coffee beans of Example 2, Sample #5, are taken prior to roasting and subjected to a decaffeination process. The decaffeination process as outlined in U.S. Pat. No. 4,474,821 to Morrison, Jr. et al. is followed to decaffeinate the beans to a point where 97% of the original caffeine level in the beans has been extracted. The beans are then roasted and ground to produce a decaffeinated roast and ground coffee having at least about 10% acrylamide reduction compared to conventionally processed products.

Example 7

Decaffeinated Roast and Ground Coffee

Green *arabica* coffee beans are decaffeinated according to the decaffeination process of U.S. Pat. No. 4,474,821 to Morrison, Jr. et al., to a point where 97% of the original caffeine level in the beans has been extracted. The decaffeinated beans are then subjected to the process outlined in Example 1 above. The resulting product is a decaffeinated roast and ground coffee having at least about 10% acrylamide reduction compared to conventionally processed products.

Example 8

Decaffeinated Roast and Ground Coffee

Green *arabica* coffee beans are decaffeinated according to the decaffeination process of U.S. Pat. No. 4,474,821 to Morrison, Jr. et al., to a point where 97% of the original caffeine level in the beans has been extracted. The decaffeinated beans are then subjected to the process outlined in Example 2 above. The resulting product is a decaffeinated roast and ground coffee having at least about 10% acrylamide reduction compared to conventionally processed products.

Example 9

Decaffeinated Roast and Ground Coffee

Coffee beans are decaffeinated by a process wherein caffeine-containing green coffee beans are concurrently extracted with a water solution of coffee solubles as is known in the art (such as that set forth in U.S. Pat. No. 3,989,850 to Erb, et al.), except that the water solution also comprises asparaginase in solution as in Example 2 above. The decaffeinated coffee removed from the extraction zone is treated to remove surface solids contained thereon and is then dried then roasted to form a decaffeinated roast and ground coffee. The level of acrylamide in the enzyme-treated roasted coffee beans, the roast and ground coffee, and coffee brews prepared therefrom is reduced by at least about 10% compared to conventionally processed products.

Example 10

Instant Coffee Product

The acrylamide-reduced roast and ground coffee produced from any of Examples 1-9 above is subjected to countercurrent extraction with heated water in a series of extraction columns at temperatures of 177° C. (350° F.) and pressures of 8 bar (120 psi) to produce a concentrated coffee extract of 20% solids. The extract is stripped of its aromatic components, and then condensed to a concentration of 60%. The aromatics are condensed and then recombined with the concentrated extract and the entire stream fed to a spray dryer where the liquid is sprayed into a countercurrent flow of heated air at 121° C. (250° F.). The final dried product is a soluble or instant coffee form having at least about 10% less acrylamide than conventionally processed products.

Example 11

Ready to Serve Sweetened Cappuccino Product

The acrylamide-reduced roast and ground coffee produced from any of Examples 1-9 above is subjected to an aqueous extraction to produce a coffee concentrate containing 7.5% solids. This concentrate is then used in the following formulation (on a weight basis) to make a ready-to-drink coffee product.

| | |
|---|---|
| Water | 50% |
| 2% low-fat milk | 35% |
| Fructose | 7% |
| Vanilla powder | 2% |
| Coffee concentrate of this invention | 6% |

These ingredients are mixed uniformly and subjected to ultra-high temperature (UHT) process conditions to sterilize the product, and then aseptically filled into individual package containers. This ready-to-drink coffee beverage has at least about 10% less acrylamide compared to conventionally processed products.

Example 12

Instant Coffee Beverage

The instant coffee produced in Example 10 is used in the following formulation (on a weight basis) to make an instant creamy coffee powder used to make a cafe latte type beverage.

| | |
|---|---|
| Instant Coffee of Example 10 | 16% |
| Foaming Creamer* | 50% |
| Sucrose | 33.5% |
| Flavors | 0.5% |

(*The foaming creamer is 68% skim milk, 30% coconut oil, 1% silicon dioxide flow agent and 1% sodium dihydrogen orthophosphate for stabilization of the protein structure during dissolution.)

The composition is prepared by weighing each of the particulate dry ingredients into a mixer and dry mixing in a paddle mixer until uniform. The resulting product is a dry instant mix that can be used to prepare a cafe latte upon addition of hot water. The dry instant mix and beverages prepared therefrom have at least about 10% less acrylamide than conventionally processed products.

Example 13

Liquid Coffee Concentrate

The acrylamide-reduced roast and ground coffee produced from any of Examples 1-9 above is subjected to an aqueous extraction with heated water in a batch extraction vessel at a temperature of 82° C. (180° F.) and a pressure of 6 bar (90 psi) to produce a concentrated coffee extract of 4.5% solids. This extract is then frozen and reconstituted with the addition of hot water to make a finished coffee beverage with 0.7% solids. The extract and the finished coffee beverage prepared therefrom have at least about 10% less acrylamide than conventionally processed products.

Example 14

Article of Commerce

The acrylamide-reduced roast and ground coffees produced from any of Examples 1-9 above are packaged in cans for sale to consumers. Printed on the cans is a message stating, "Acrylamide-free product!"

Example 15

Article of Commerce

Green coffee beans treated with enzyme according to any of Examples 1-9 above are packaged in drums. The drums are labeled, "Low in Asparagine."

Example 16

Article of Commerce

The ready to serve sweetened cappuccino product of Example 11 is packaged in a bottle for sale to consumers. A label on the bottle states, "Acrylamide reduced by over 90%!" A television commercial for the product communicates the message, "Acrylamide-reduced product."

Example 17

Article of Commerce

Brewed coffee made from roast and ground coffee of any of Examples 1-9 above is sold to consumers served in a cup. A sign posted inside the retail establishment where the brewed coffee is sold communicates the message, "We serve only acrylamide-free coffee."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for reducing the level of acrylamide formation in coffee beans which comprise soluble materials and asparagine using an asparaginase-reducing enzyme, said method comprising the step of extracting at least a portion of asparagine from said coffee beans to form an extract, contacting said extract with said enzyme for a sufficient amount of time to reduce the level of asparagine at least about 10%, and adding back at least a portion of said extract comprising said soluble materials to at least a portion of said coffee beans, followed by roasting said beans.

2. A method according to claim 1 which employs a dominant bath comprising said enzyme, whereby soluble materials in said beans, with the exception of said asparagine, do not continue to extract out of said beans, once equilibrium has been reached.

* * * * *

UNITED STATES PATENT AND TRADEMARK OFFICE
CERTIFICATE OF CORRECTION

PATENT NO.        : 7,220,440 B2                                        Page 1 of 1
APPLICATION NO.   : 10/603973
DATED             : May 22, 2007
INVENTOR(S)       : Dria et al.

It is certified that error appears in the above-identified patent and that said Letters Patent is hereby corrected as shown below:

Column 4
Line 32, delete "un-decaffeiniated" and insert -- un-decaffeinated --.

Column 8
Line 23-24, delete "calorimeter" and insert -- colorimeter --.

Column 15
Line 48, delete "HPI,C" and insert -- HPLC --.

Signed and Sealed this

Eighth Day of July, 2008

JON W. DUDAS
*Director of the United States Patent and Trademark Office*